Figure 3:
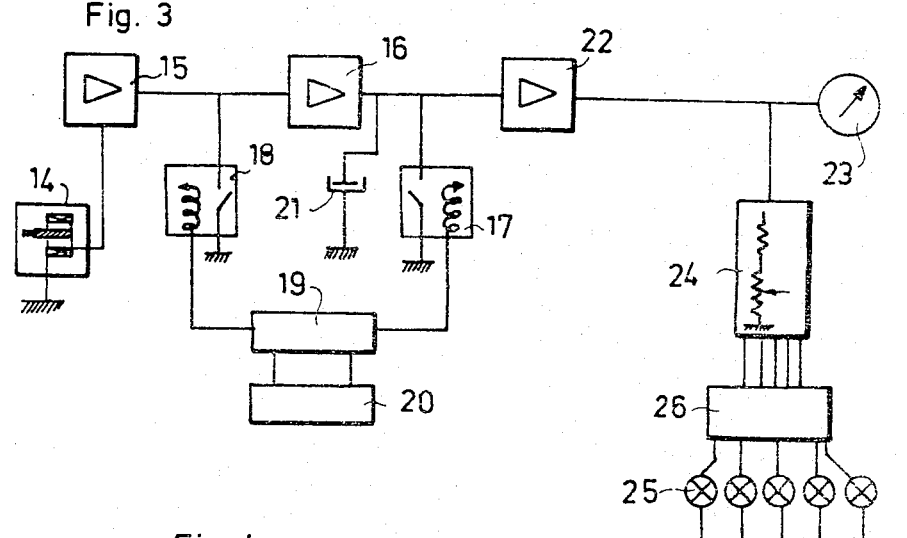

United States Patent [19]

Bourdeau et al.

[11] Patent Number: 4,470,810
[45] Date of Patent: Sep. 11, 1984

[54] TEST PROCEDURE FOR THE DYNAMIC MEASUREMENT OF DENTAL MOVABILITY AND IMPLEMENTING INSTRUMENTATION

[75] Inventors: Charles Bourdeau; René Fadel, both of Tolosan; Edmond Benque, Toulouse; Bernard Joniot, Toulouse; Gérard Paloudier, Toulouse, all of France

[73] Assignee: Centre National de la Recherche Scientifique (CNRS), Paris, France

[21] Appl. No.: 382,122

[22] Filed: May 26, 1982

[30] Foreign Application Priority Data

May 26, 1981 [FR] France .................................. 81 10679

[51] Int. Cl.$^3$ ............................. A61C 3/00; A61B 5/10
[52] U.S. Cl. ..................................... 433/72; 33/174 D; 433/215
[58] Field of Search ...................... 433/27, 32, 72, 215; 73/11, 82; 33/174 D

[56] References Cited

U.S. PATENT DOCUMENTS

| | | | |
|---|---|---|---|
| 3,421,364 | 1/1969 | Moneypenny et al. | 73/82 |
| 3,722,100 | 3/1973 | Weisman et al. | 433/72 |
| 3,943,913 | 3/1976 | Johnson | 33/174 D X |
| 4,111,039 | 9/1978 | Yamawaki et al. | 73/82 X |

FOREIGN PATENT DOCUMENTS

| | | | |
|---|---|---|---|
| 2452578 | 5/1976 | Fed. Rep. of Germany | 433/72 |
| 874051 | 10/1981 | U.S.S.R. | 433/215 |

Primary Examiner—Robert P. Swiatek
Attorney, Agent, or Firm—Shlesinger, Arkwright, Garvey & Fado

[57] ABSTRACT

A dynamic procedure to measure the movability of teeth wherein a given motion is applied to a tooth to cause a displacement and wherein the average displacement rate of the tooth is measured. The instrument implementing this procedure comprises means (4–8) for generating the given motion, means for releasing said given motion, (10–12), and means (13) for transmitting this given motion to the tooth. The tooth displacement is measured by a magnetic pickup (14) emitting an electric signal representing the tooth displacement to an electronic data-processing and display circuit.

18 Claims, 5 Drawing Figures

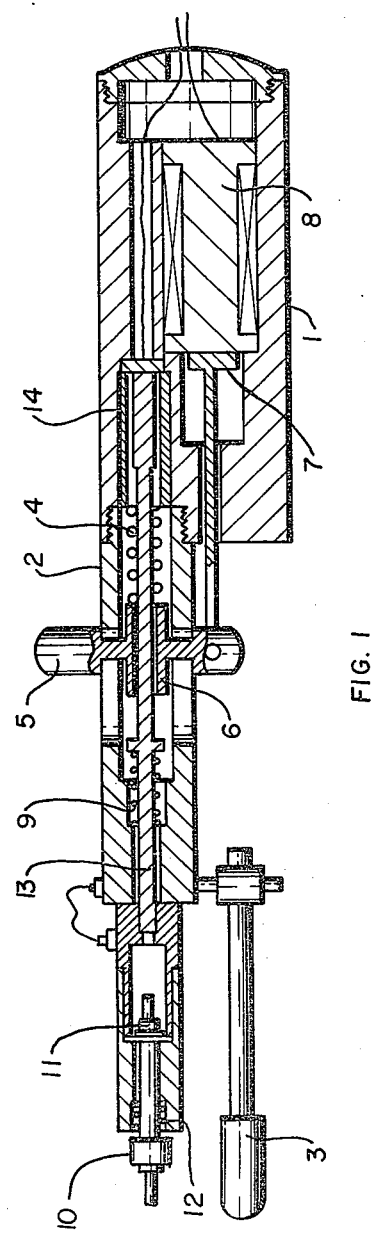
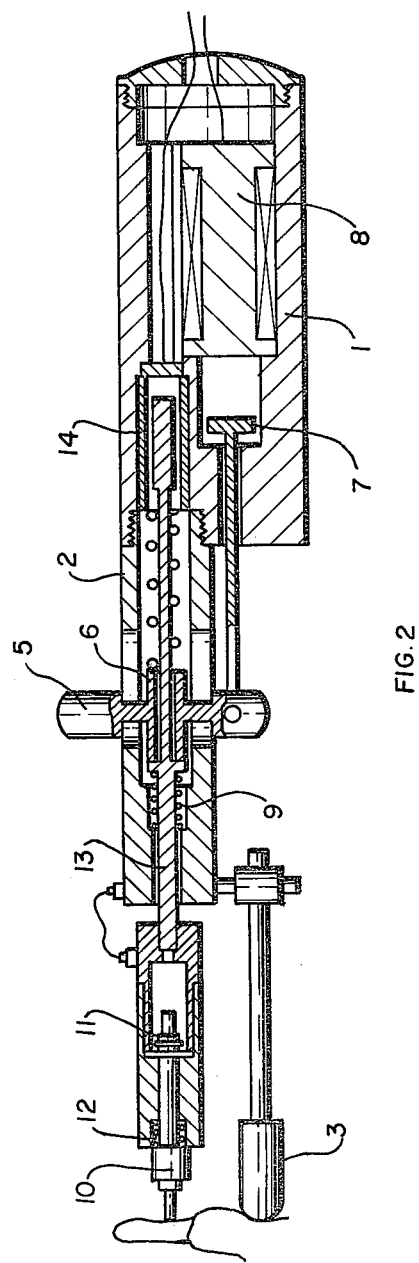
FIG. 1
FIG. 2

TEST PROCEDURE FOR THE DYNAMIC MEASUREMENT OF DENTAL MOVABILITY AND IMPLEMENTING INSTRUMENTATION

The present invention relates to a procedure for measuring the movability of teeth and to an implementing instrument.

Gum shrinkage increases tooth movability. Beyond a given threshold, the teeth must be treated if their loss by falling out is to be avoided within a relatively brief time. In order to ascertain the most appropriate therapy and thereupon to assess its effectiveness, the movability of the affected teeth must be measured.

Now there is not at present a device allowing an accurate and simple evaluation of this parameter. Several costly and bulky apparatus have been developed in research centers, but they present difficulties is use, even to experts (for instance the U.S. Pat. No. 4,034,476). The generally adopted principle is a static measurement of the tooth displacement when subjected to a constant load which is applied perpendicularly to its outer vertical side. Such apparatus include a dynamometer and a comparator. Considering that the measured displacements are very slight (from several microns to several millimeters), such apparatus requires being fixed in extremely rigidly manner to the jaw.

The complexity of such apparatus and their operational difficulties have hampered their industrial development, and presently tooth movability is practically assessed by estimating their displacement due to a manual operation.

Such lack of accuracy in measurement foregoes any possible use of a movability scale whereby to define in reliable and accurate manner which treatment should be applied to the particular case.

It is the object of the present invention to remedy these insufficiencies of the known techniques by providing a dynamic test procedure for the dental movability which can be implemented quickly and simply, and by providing also an instrument to carry out this procedure that does not require fastening to the jaw.

Another object of the present invention is to provide an accurate and faithful test instrument operative in spite of sometimes difficult testing conditions.

Another object of the present invention is to provide a test instrument of moderate cost and compact size requiring only average dexterity which is typical and normal of a dental practitioner.

Another object of the present invention is to make it possible to use a movability scale of at least four ranges which can be defined in non-restrictive manner as follows:

movability I: healthy teeth (less than 0.1 mm displacement)
movability II: teeth of which the displacement can be detected upon being manually loaded (displacement between 0.1 and 0.5 mm)
movability III: highly movable teeth (displacement between 0.5 and 1 mm)
movability IV: teeth to be extracted.

To that end, the test procedure of the present invention consists in:
generating a given motion,
transmitting this motion directly to a tooth of which the movability is to be measured so as to cause a displacement of said tooth, and
measuring the tooth's rate of displacement during this displacement.

In a preferred mode of implementation, the speed measurement is performed by measuring the average displacement rate of the tooth during a given time interval less than the time the tooth is being displaced.

The average displacement rate can be measured by generating a signal representing said displacement, by amplifying this signal, and by measuring the amplitude variation of the amplified signal during a constant time interval which in particular shall be between 0.1 and 1.5 ms, preferably about 1 ms. Thus a voltage proportional to the tooth displacement during this time interval is actually measured, and hence a voltage which is proportional to the average displacement rate. The time interval is selected to be long enough for the measurement to be significant, and also short enough to by pass spurious information due to the operator moving his arms.

The invention also applied to a device or instrument for implementing said procedure, said instrument comprising:
means designed to generate a given motion,
means for transmitting said motion to a tooth of which the movability must be ascertained,
holding and release means designed to initiate the generating means in order to permit producing said motion and its transfer to said transmission means,
means measuring the average tooth displacement rate within a predetermined time interval,
and display means for the test results.

Other features of the test procedure and of the instrument of the present invention will be shown in the description below in relation to the attached drawings which are provided in illustrative and non-restrictive manner.

Figure 4:
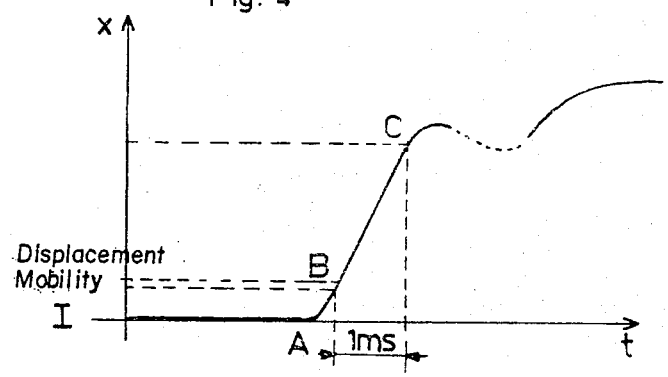
Figure 5:
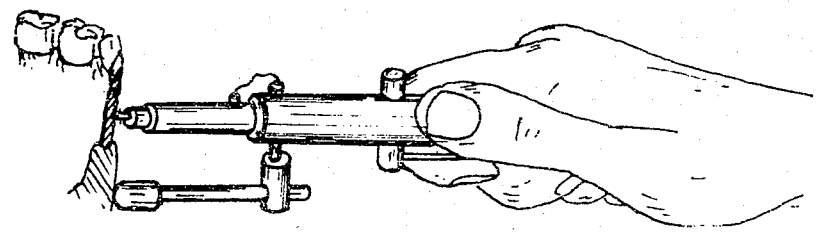

FIG. 1 is a cross-section of the mechanical and electromechanical part of the test instrument of the present invention when in the cocked position, FIG. 2 is a cross-sectional view of the same part when in the initiated position, FIG. 3 is a block diagram of the electronics of the instrument of the present invention, FIG. 4 illustrates a graph of a tooth displacement as a function of time, and FIG. 5 illustrates the operation of the device to carry out the dynamic measurement of tooth movability.

The instrument illustratively shown in FIG. 1 and 2 comprises a body 2 consisting of a hollow cylinder to the rear of which is fixed a muff 1 used to keep the instrument in place. An end means 3 is fastened to the fore and outside of body 2 to rest on the hard part of the gum at a location plumb with the tooth being inspected. However this end means merely is an aid in positioning the instrument and in no way is mandatory.

Means generating a given motion are provided within the hollow cylinder 2 and comprise a calibrated spring 4 and also means for cocking this spring 4 and means for holding said cocking means. These cocking means consist of a trigger 5 solidly joined to a slider 6 of which the displacement generates the compression of the calibrated spring 4. A bolt 7 also is solidly joined to the slider 6 and forms the armature of an electromagnet 8, this bolt 7 being capable of keeping the spring 4 compressed when the electromagnet 8 is energized. The spring 4 is calibrated by means of a mating spring 9 of which the compression force can be adjusted.

Means for initiating the motion are provided at the fore of the cylinder 2 and include a sensor 10 which the operator places against the tooth being inspected. This sensor 10 is machined on the inside in a manner to achieve an annular micro-switch 11. A small and very compliant spring 12 keeps the sensor 10 to the fore when in the rest position, thereby assuring the closure of the microswitch. The microswitch 11 breaks the electric supply line to the electromagnet 8 which maintains the cocking.

A piston 13 is provided between the sensor 10 and the slider 6 to ensure the transmission of the motion which is applied to it by the slider 6 when the spring 4 is released.

The moment the sensor 10 makes contact with the inspected tooth, the microswitch opens and causes the supply circuit to the electromagnet 8 also to open, thereby releasing the bolt 7. The spring 4 expands, driving the slider 6 which imparts said given motion to the piston 13. This motion is transmitted to the inspected tooth by the piston 13 and causes the tooth to be displaced.

Under the action of the impulse transmitted by the piston 13, the tooth more or less moves back depending on the condition of the ligaments of the alveolar wall. The rate at which the tooth moves back reflects this condition and the measurement of this rate allows accurately determining the movability of the tooth. To measure this rate, the tooth displacement is measured during a given time interval ascertained by a magnetic pickup 14 associated with the piston 13. The pickup 14 delivers an electric signal with an amplitude proportional to the tooth displacement and consequently to its average speed provided this amplitude be always measured at the end of a constant time interval.

The mating spring 9 arranged between the front wall of the body 2 and a stop means on the piston 13 not only provides the calibration of the spring 4 but also returns the piston 13 into its rest position (FIG. 1) after the given motion has been imparted.

The assembly of the mechanical and electromechanical elements listed above is arranged in a casing designed to be of the general shape and size of a fountain pen.

FIG. 3 shows the electronic data processing device for the information obtained from the magnetic pickup 14. This device comprises an amplifier 15 designed to make the signal from the magnetic pickup 14 operative. The amplified signal then is fed to a maximum amplifier 16 controlled by two switches 17 and 18, whereby operator motions are eliminated as a factor and the error introduced by the pullback of his arm is minimized.

The switch 17 is actuated by a threshold detector 19 and resets to zero a memory device of the maximum amplifier 16 the moment the pickup 14 shows a displacement slightly less than that corresponding to a physiological movability (movability I). This pickup also triggers an adjustable monostable device 20. The monostable device 20 opens the switch 18 connecting the input of the maximum amplifier 16 to ground. The monostable device 20 is adjusted for a time corresponding to the response-time of the "tooth-piston-ressort" set. At the end of this time, the monostable device 20 flips, closing the switch 18 and applying a zero potential to the maximum amplifier 16 which then feeds a voltage proportional to the tooth displacement during the time interval determined by the monostable device 20 to the memory device, said voltage therefore being proportional to the average rate of displacement during this time. The memory device consists of a capacitor 21 of which the charge accumulated during the time determined by the monostable device 20 therefore is a function of the average rate of displacement of the tooth during this time.

This voltage then is amplified in a circuit 22 either for direct read-off from a galvanometer 23 or for its comparison with reference potentials in a circuit 24 commanding the threshold detector 26. This threshold detector 26 controls the supply to pilot lights 25 each corresponding to a movability range.

An example of the time-function of a tooth displacement as measured by the magnetic pickup 14 is shown in FIG. 4. In this figure, the time origin corresponds to the opening of the microswitch 11. The moment the piston 13 imparts to the tooth the given motion produced by the spring 4 and the slider 6 (point A), the tooth begins to move and with it the piston 13 and the movable part of the magnetic pickup 14. This pickup 14 then emits a signal fed to the electronics. The moment the amplitude of this signal reaches a threshold (point B) slightly below the signal amplitude corresponding to the movability I of the above-defined scale, the threshold detector 19 actuates the switch 17 and triggers the monostable device 20. This is the origin of the time intervals measuring the rate. The capacitor 21 then charges until the monostable device 20 will flip (point C) and closes the switch 18. The capacitor charge therefore is a function of the displacement rate of the tooth within the time interval determined by the monostable device 20.

However the difficulty in measuring is that the given motion applied to the tooth is not wholly absorbed in it by its backward motion. The non-absorbed motion causes the operator's arm to move back, and the measurement beyond point C loses any significance. This difficulty is overcome on one hand by calibrating the duration of the time-interval of rate-measurement, corresponding to the maximum time allowing a tooth of the highest movability (movability IV) to reach its maximum displacement, and on the other hand by calibrating means for generating a given motion such that the pullback rate of the arm be negligible with respect to that of the tooth. Experiments performed on various patients have shown that free-hand measurements, without resting on the gum by the end means 3, provide accurate and faithful results. In particular the device of the invention makes it possible to inspect teeth to the rear of the jaw and which would be inaccessible to bulkier instruments. Furthermore, the measurements can be taken both on the front and on the rear sides of the teeth.

Movability display can be carried out on a separate casing containing the electronics or directly on the body of the measuring pickup using luminous displays or electroluminescent diodes.

To carry out the measurements under good conditions, it is necessary that the impact point of the sensor 10 be located at a constant distance from the pivoting point of the tooth so that a constant torque be exerted on this tooth. This site is located at approximately ⅔ of the height of the tooth starting from the gum. Moreover, one may provide an antiskid pad fastened to the end of the sensor to prevent sidewise slippage of the instrument.

Obviously the above description was provided in a merely illustrative and non-restrictive manner and numerous modifications can be introduced without thereby transcending the scope of the present invention. For instance the means releasing the given motion may be mechanical, even though such a solution demands greater operator dexterity. Similarly, the microswitch 11 may be replaced by a less fragile opticoelectronic window. Again any mechanical, electro-mechanical or other means may be used to produce the given motion required to cause tooth displacement.

Lastly other modification may be introduced as the present invention is not restricted to the above description but on the contrary covers all its variations.

We claim:

1. A dynamic test procedure for tooth movability, comprising the steps of:
   (a) imparting a movement to a pre-selected tooth by means of an instrument;
   (b) displacing said tooth thereby;
   (c) measuring with measuring means associated with said instrument an average displacement rate of said tooth during a time interval less than the total time said tooth is being displaced; and,
   (d) comparing said measured displacement rate with a standard whereby said tooth condition may be determined.

2. A dynamic test procedure for tooth moveability as defined in claim 1, further comprising the steps of:
   (a) generating an electrical signal proportional to said average displacement rate;
   (b) amplifying said signal; and,
   (c) measuring said amplified signal amplitude variation during a known constant time interval.

3. A dynamic test procedure for tooth moveability as defined in claim 2, wherein:
   (a) said time interval ranges from between 0.1 milliseconds to 1.5 milliseconds.

4. An instrument for tooth movability, comprising:
   (a) electrically activated means for holding a displaceable portion of said instrument;
   (b) means associated with said instrument for placing said instrument proximate a pre-selected tooth;
   (c) means for releasing said portion when at least a portion thereof contacts said pre-selected tooth at a pre-selected point on said tooth whereby said tooth is displaced;
   (d) means associated with said instrument for measuring said tooth average displacement rate during a pre-determined time interval less than the total time said tooth is displaced; and,
   (e) means for displaying said average displacement rate.

5. An instrument for measuring tooth movability as defined in claim 4, wherein:
   (a) said holding means being associated with said releasing means;
   (b) said holding and releasing means include:
      i. cocking means for holding a first calibrated spring under tension; and,
      ii. a slider displaceably connected to said spring as a means for displacing said tooth when said spring is released by said cocking means.

6. An instrument for measuring tooth moveability as defined in claim 5, further comprising:
   a. a mating spring axially aligned with said first spring and adapted for having the capability of adjusting the tension of said mating spring as a means for calibrating the tension of said first spring.

7. An instrument for measuring tooth moveability as defined in claim 5, wherein:
   a. said cocking means includes a trigger disengageably connected to said slider.

8. An instrument for measuring tooth moveability as defined in claim 5, wherein:
   a. said holding means comprises a displaceable armature of an electromagnet connected to said slider as a means for holding said slider when said magnet is energized.

9. An instrument for measuring tooth moveability as defined in claim 8, wherein:
   a. said release means includes a means for de-energizing said electromagnet for releasing said slider.

10. An instrument for measuring tooth moveability as defined in claim 9, wherein:
    a. said release means includes a contact activated microswitch for de-energizing said electromagnet.

11. An instrument for measuring tooth moveability as defined in claim 10, wherein:
    a. said microswitch has a contact end and a force receiving end;
    b. a sensor for contacting said tooth and transmitting said force to said tooth is connected to said microswitch contact end; and,
    c. a piston is displaceably connected to said slider and connected to said force receiving end as a means for transmitting said force to said sensor.

12. An instrument for measuring tooth moveability as defined in claim 11, further comprising:
    a. a magnetic pick-up means connected to said piston and adapted for generating an electrical signal proportional to said displacement rate.

13. An instrument for measuring tooth moveability as defined in claim 12, further comprising:
    a. an amplifier;
    b. a threshold detector connected to said amplifier;
    c. two switches, one mounted on one side of said detector and the other mounted on the other side of said detector; and,
    d. a mono-stable device connected to said threshold connector and adapted for generating a electrical signal proportional to said displacement rate.

14. An instrument for measuring tooth moveability as defined in claim 13, further comprising:
    a. display means connected to said monostable device for displaying said average displacement rate.

15. An instrument for measuring tooth moveability as defined in claim 14, wherein:
    a. said display means includes a galvanometer.

16. An instrument for measuring tooth moveability as defined in claim 15, wherein:
    a. said display means further includes means for comparing said average displacement rate electrical signal to a known base rate signal; and,
    b. pilot lights connected to said comparing means and adapted for displaying said average displacement rate.

17. An instrument for measuring tooth moveability as defined in claim 4, further comprising:
    a. a hollow casing of the general shape and size of a fountain pen for holding said instrument.

18. An instrument for measuring tooth movability, comprising:
    (a) means for holding and releasing a given force;
    (b) means for imparting said force to a pre-selected tooth at a pre-selected point on said tooth for thereby causing said tooth to be displaced;
    (c) means for measuring said tooth average displacement rate during a pre-determined time interval;

(d) means for displaying said average displacement rate;
(e) said holding and releasing means include:
   i. cocking means for holding a first calibrated spring under tension; and,
   ii. a slider displaceably connected to said spring as a means for transmitting said force when said spring is released by said cocking means; and,
(f) said holding means comprises a displaceable armature of an electromagnet connected to said slider as a means for holding said slider when said magnet is energized.

* * * * *